United States Patent [19]

Jamshidi

[11] 3,938,505

[45] Feb. 17, 1976

[54] SOFT TISSUE BIOPSY ASPIRATING DEVICE

[76] Inventor: Khosrow Jamshidi, 610 Winston Court, St. Paul, Minn. 55118

[22] Filed: Mar. 27, 1975

[21] Appl. No.: 562,915

Related U.S. Application Data

[63] Continuation of Ser. No. 497,903, Aug. 16, 1974, abandoned, which is a continuation-in-part of Ser. No. 330,320, Feb. 7, 1973, abandoned, which is a continuation-in-part of Ser. No. 261,818, June 12, 1972, abandoned.

[52] U.S. Cl............. 128/2 B; 128/218 C; 128/347; 128/329 R
[51] Int. Cl.².................................. A61B 10/00
[58] Field of Search........... 128/2 B, 2 R, 310, 329, 128/347, 278, 218 C

[56] References Cited
UNITED STATES PATENTS

| | | | |
|---|---|---|---|
| 2,373,520 | 4/1945 | Wallin | 128/218 C |
| 2,739,588 | 3/1956 | Yochem | 128/218 C |
| 2,844,148 | 7/1958 | Raife | 128/218 C |
| 2,869,541 | 1/1959 | Helmer et al. | 128/218 C |
| 3,330,268 | 7/1967 | Goldsmith | 128/2 B |
| 3,470,867 | 10/1969 | Goldsmith | 128/2 B |
| 3,577,980 | 5/1971 | Cohen | 128/2 F |
| 3,727,602 | 4/1973 | Hyden et al. | 128/2 B |

FOREIGN PATENTS OR APPLICATIONS

| 587,586 | 1/1959 | Italy | 128/2 B |
|---|---|---|---|

OTHER PUBLICATIONS
The Lancet, Oct. 10, 1964, p. 794.

Primary Examiner—Kyle L. Howell
Attorney, Agent, or Firm—Orrin M. Haugen

[57] ABSTRACT

A biopsy aspirating device for gathering soft tissue samples comprising a syringe having a barrel, with a plunger sealingly received within the barrel to form a chamber with a controllably variable volume, and with a hollow sample-receiving needle mounted on a needle mounting boss attached to the barrel. The needle mounting boss has a bore formed therein to provide communication between the needle bore and the barrel with sample blocking means having an abutment surface thereon being provided to engage the sample and retain the sample in a position to prevent direct contact between the sample and the bore formed in the boss. The plunger is secured to the conventional gripping shaft, and the gripping shaft has means for releasably engaging the proximate end of the barrel at controllable axial dispositions therealong. In use, the needle is used to puncture the body, and the tip of the needle is advanced until it reached a point adjacent the organ from which the tissue is to be collected. At this point, the plunger is withdrawn and locked into engagement with the barrel, so as to form a partial vacuum within the barrel. The advancement of the needle is continued, thereby gathering a sample of tissue from the desired organ, with the tissue sample moving into the needle shank until contact is made with the abutment surface.

6 Claims, 20 Drawing Figures

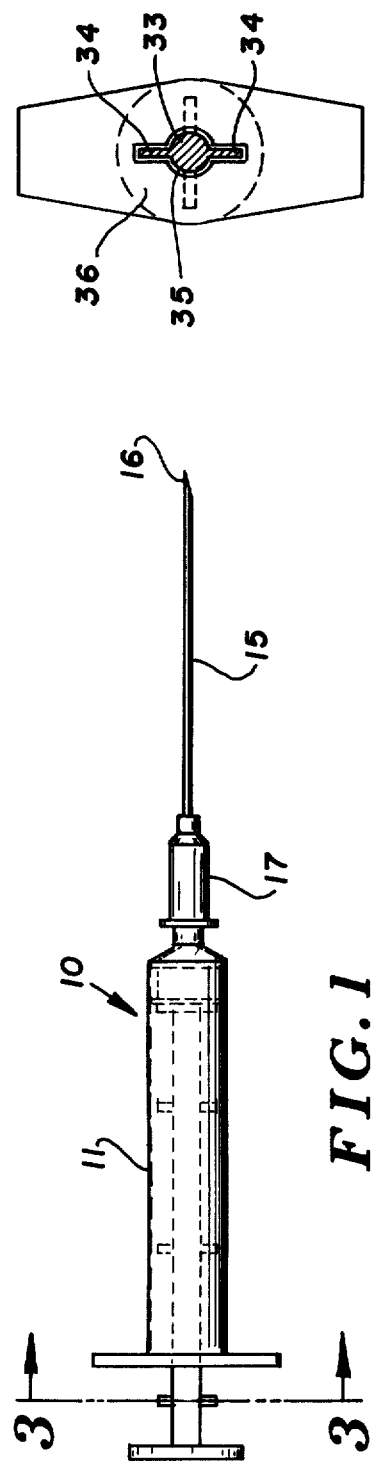
FIG. 1
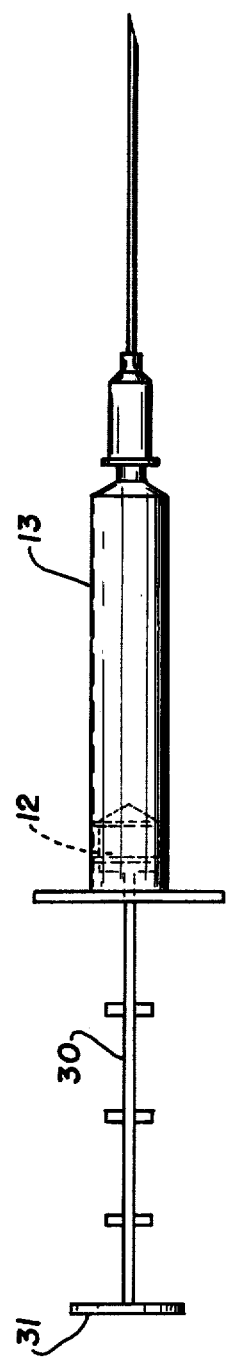
FIG. 2
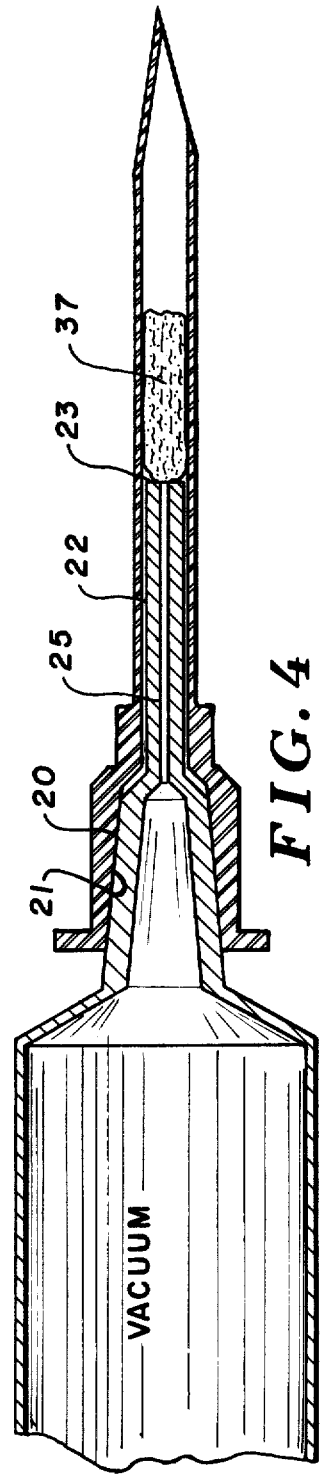
FIG. 3
FIG. 4

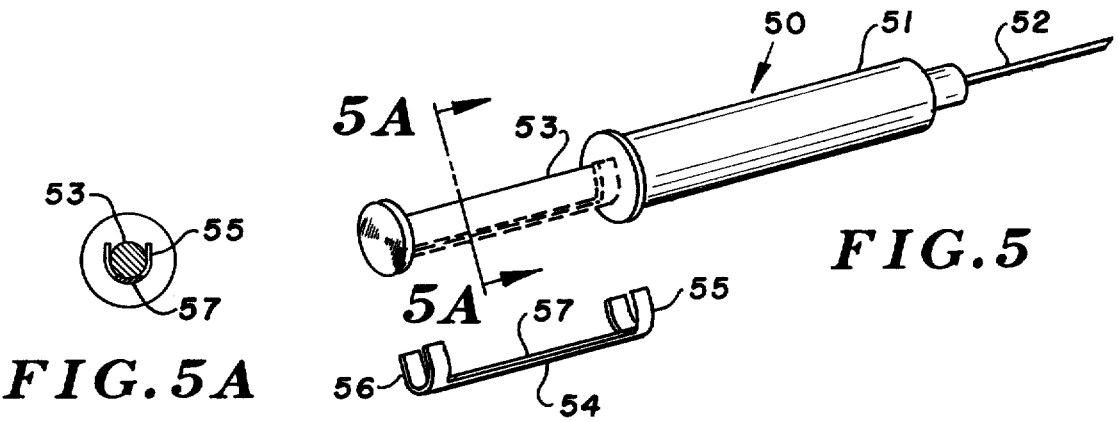
FIG.5
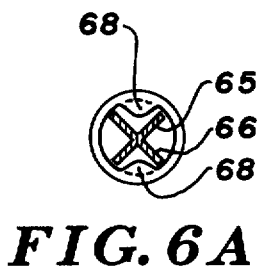
FIG.5A
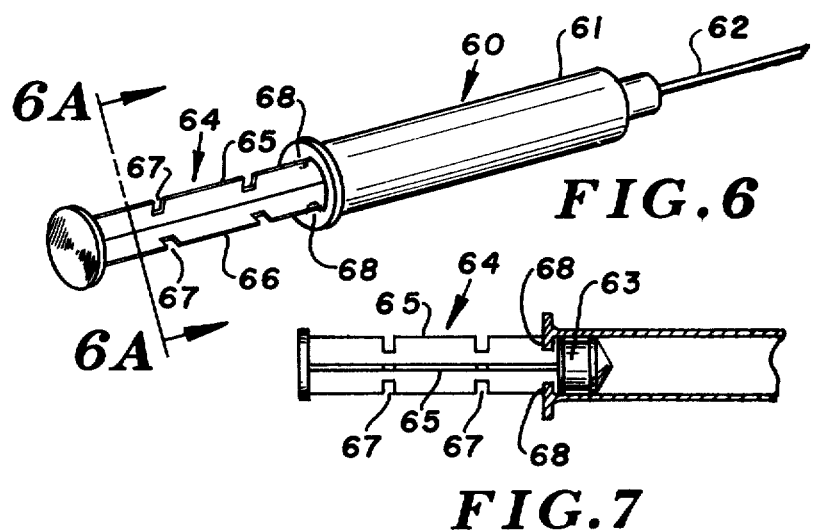
FIG.6
FIG.7
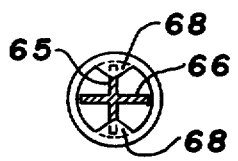
FIG.6A
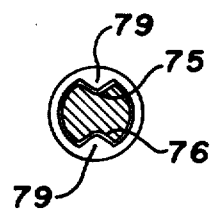
FIG.6B
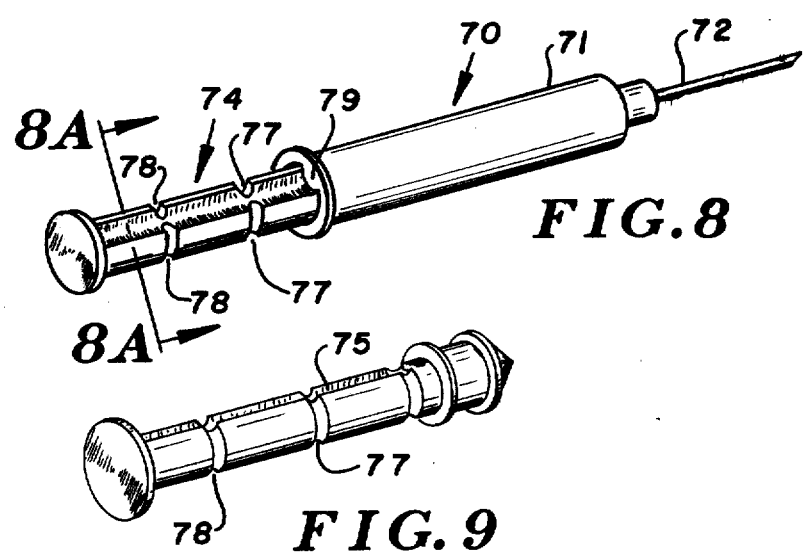
FIG.8
FIG.8A
FIG.9

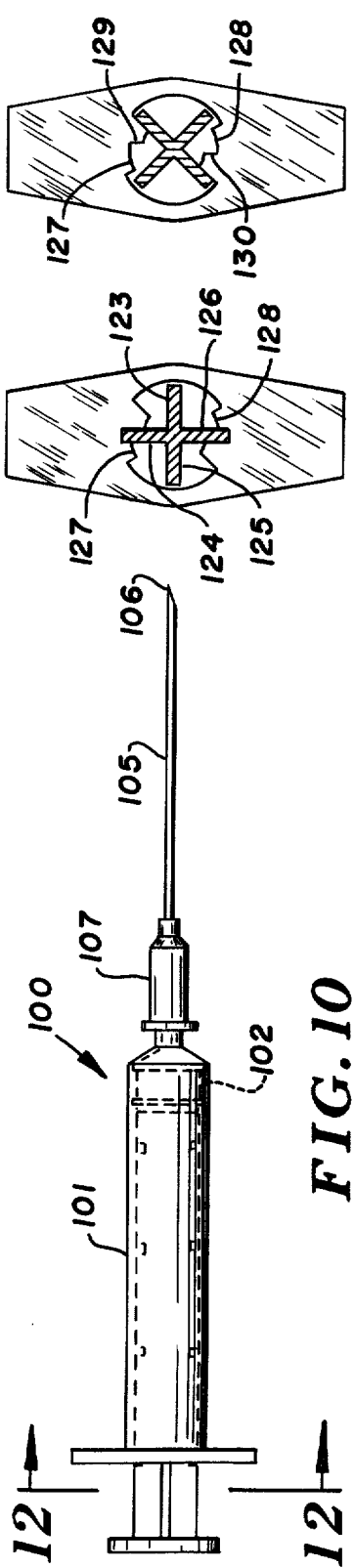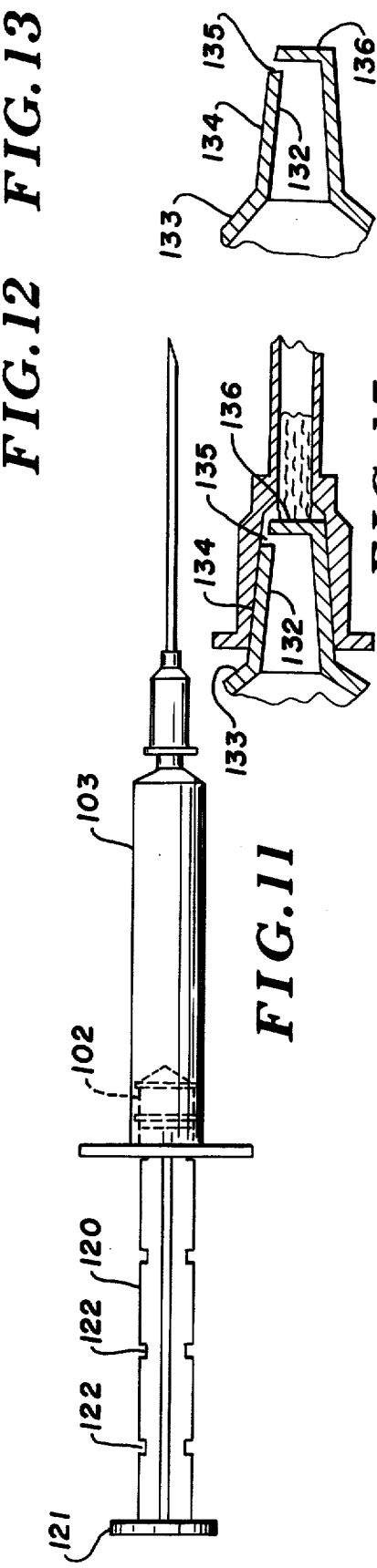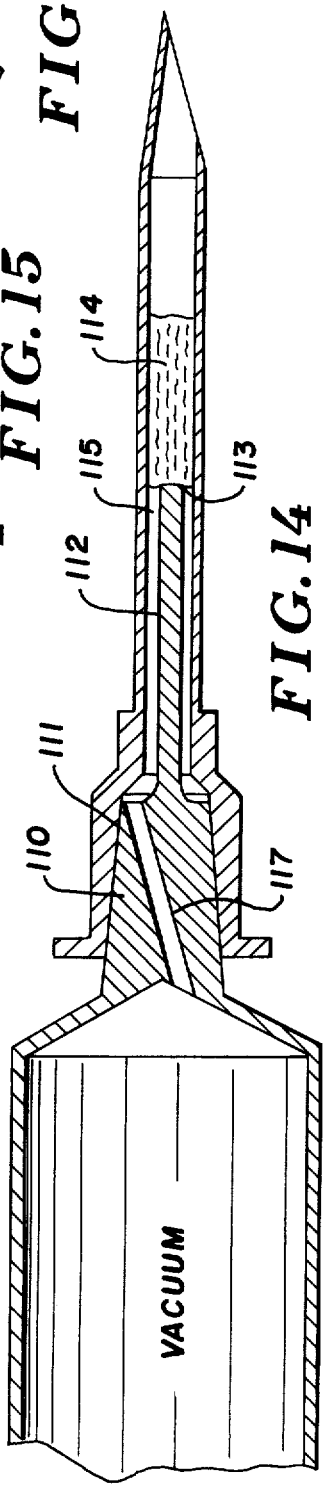

SOFT TISSUE BIOPSY ASPIRATING DEVICE

This is a continuation of application Ser. No. 497,903, filed Aug. 16, 1974, now abandoned, which was a continuation-in-part application of Ser. No. 330,320, filed Feb. 7, 1973, now abandoned, and which application was a continuation-in-part of application Ser. No. 261,818, filed June 12, 1972, now abandoned.

BACKGROUND OF THE INVENTION

The present invention relates generally to an improved biopsy aspirating device for obtaining tissue samples, and more particularly, to an improved biopsy aspirating device particularly designed to gather tissue samples of soft tissue organs, such as liver, kidney, spleen, thyroid or the like. The apparatus of the present invention is particularly adapted to obtain tissue samples without requiring unusual surgical procedures, and without requiring that large openings be formed within the body; and is further adapted to retain such samples without exposing the sample structure to risk of damage due to the exertion of unusual forces upon the substance of the tissue sample.

At the present time, a variety of specific biopsy instruments are being utilized for obtaining biopsy test specimens from various organs, however, such instruments are normally cumbersome when being utilized for obtaining biopsy specimens from internally disposed organs which tend to bleed profusely when specimens are removed therefrom. It is deemed desirable, therefore, to utilize a device which reduces the complexity of the procedure for the operator, thereby reducing the risk of complications resulting therefrom; and also to utilize apparatus which neither damages nor destroys the specimen when obtained.

SUMMARY OF THE INVENTION

Briefly, in accordance with the present invention, a biopsy aspirating device is provided which is specifically adapted for gathering soft tissue samples, and comprises a syringe having a barrel, a plunger which is sealingly received within the barrel to form a chamber with a controllably variable volume, and with a sample receiving hollow needle having a sharpened tip being disposed on the end of the barrel. The syringe is provided with needle mounting boss means for being received within the hub of the needle, with a bore being formed in the boss to provide communication between the needle bore and the barrel chamber with sample blocking means having an abutment surface thereon being provided along the boss to engage the sample and retain the sample in a position to prevent direct contact between the sample and the bore formed in the boss. The plunger is provided with a gripping shaft having locking means for retaining the plunger at a point removed from the base of the barrel, so as to maintain a controlled partial vacuum within the chamber. In use, the needle is inserted into the patient until the distal tip is disposed immediately adjacent the organ from which the sample is to be obtained. The plunger is then withdrawn or retracted within the barrel and locked in place so as to create an maintain a partial vacuum within the chamber. With the plunger retained in locked disposition, the needle is immediately advanced until the tip penetrates the organ, and when advancement ceases, the partial vacuum present in the chamber will extract the sample from the organ and draw it further into the needle bore until contact is made with the abutment surface. The abutment surface formed at the tip of the projection of the needle mounting boss prevents the sample from passing along the length of the needle and into contact with the opening of the bore formed in the boss, thereby preserving the integrity of the sample at a point within the needle bore and inwardly from the needle tip. If desired, after removal of the biopsy needle, a cauterizing device or cryoprobe may be inserted into the opening formed by the needle for the purpose of cauterizing the wound formed along the biopsy track.

Therefore, it is a primary object of the present invention to provide apparatus and technique for obtaining biopsy samples or specimens from soft tissue organs such as liver, kidney, spleen or the like, with means being provided for controllably positioning the sample against an abutment surface, thereby maintaining the integrity of the sample while continuously subjecting the sample to an aspirating force.

It is a further object of the present invention to provide apparatus and technique for obtaining biopsy samples or specimens from soft tissue organs pursuant to a simplified technique and without requiring those moderately extensive surgical procedures which may at times be required.

It is yet a further object of the present invention to provide improved apparatus and technique for obtaining biopsy samples or specimens from soft tissue organs wherein the sample is maintained in a condition free from exposure to unusual forces.

Other and further objects of the present invention will become apparent to those skilled in the art upon a study of the following specification, appended claims, and accompanying drawings.

BRIEF DESCRIPTION OF THE DRAWINGS

FIG. 1 is a side elevational view of the biopsy aspirating device fabricated in accordance with the present invention, and showing, in phantom, the disposition of the plunger and its gripping handle partially removed from the base of the barrel;

FIG. 2 is a view similar to FIG. 1 and showing the disposition of the plunger when removed a substantial distance from the base of the barrel;

FIG. 3 is an elevational view of the proximate end of the apparatus shown in FIGS. 1 and 2;

FIG. 4 is a detail sectional view, on a slightly enlarged scale illustrating the needle portion of the structure with a biopsy sample present in the needle bore, and with the barrel portion being shown partially broken away;

FIG. 5 is an exploded perspective view of a modified form of biopsy aspirating device structure and illustrating the structure of the device per se and a retained rod element which may be utilized to releasably hold the plunger in a predetermined disposition;

FIG. 5A is a vertical sectional view taken along the line and in the direction of arrows 5A—5A of FIG. 5;

FIG. 6 is a perspective view of an additional modification of the biopsy aspirating device;

FIGS. 6A and 6B are vertical sectional views taken along the line and in the direction of arrows 6A—6A of FIG. 6 and illustrating the plunger in open and locked positions respectively;

FIG. 7 is a vertical sectional view, partially broken away, taken through the diameter of the barrel, and illustrating the barrel and plunger assembly of the structure shown in FIG. 6;

FIG. 8 is a perspective view of a further modification of the biopsy aspirating device of the present invention;

FIG. 8A is a vertical sectional view taken along the line and in the direction of the arrows 8A—8A of FIG. 8;

FIG. 9 is a perspective view of the gripping shaft and plunger portion of the structure illustrated in FIG. 8;

FIG. 10 is a side elevational view of a modification of the biopsy aspirating device illustrated in FIGS. 1–5;

FIG. 11 is a side elevational view of the device shown in FIG. 10, but with the plunger being removed a substantial distance from the base of the barrel;

FIG. 12 is a sectional view taken along the line and in the direction of the arrows 12—12 of FIG. 10, and illustrating the disposition of the rod element when locked within the barrel to releasably hold the plunger in a predetermined disposition;

FIG. 13 is a sectional view similar to FIG. 12 and illustrating the plunger in unlocked disposition;

FIG. 14 is a detail sectional view, on a slightly enlarged scale, illustrating a modified form of the structure with a biopsy sample being present in the needle bore, and with the barrel portion being shown partially broken away;

FIG. 15 is a fragmentary detail sectional view showing a still further modified form of the structure with a bore and abutment surface being formed inwardly at the base of the boss; and FIG. 16 is a view similar to FIG. 15 and illustrating the structure with the needle being removed therefrom.

DESCRIPTION OF THE PREFERRED EMBODIMENTS

In accordance with the preferred embodiments of the present invention, particular attention is initially directed to FIGS. 1–4 of the drawings wherein one modification of the structure is illustrated in detail. Essentially, the biopsy aspirating device generally designated 10 includes a barrel member 11 having a plunger 12 sealingly received within the barrel and forming a chamber zone as at 13. A sample-receiving hollow needle 15 is provided having a sharpened tip 16 and a mounting hub 17 for locking onto the tip and of the barrel 11 with the sample-receiving hollow needle 15 having a shank portion interposed between the sharpened tip 16 and the mounting hub 17. The tip end of the barrel 11 is compressible for grippingly engaging the inner diameter of the mounting hub 17 of hollow needle 15.

In other words, a needle mounting boss means 20 is arranged at the distal or tip end of barrel 11, with the boss means 20 extending from the barrel with needle hub-receiving surface 21 being disposed therealong. In addition, the boss 20 includes a projecting tip means 22 having an abutment surface 23 arranged at the free distal end thereof. In the modification illustrated in FIGS. 10–14 inclusive, the abutment surface is arranged along a generally flat or planar zone disposed at the free distal end of the boss means so as to provide a "blocking surface" which avoids exposing the tissue sample to an unusual concentration of forces or pressures. This feature will be discussed in detail hereinafter. In the embodiment illustrated in FIGS. 1–4 of the drawings, a continuous bore 25 extends through the members 20 and 22 to provide communication between the interior of the needle 15 and the chamber 13.

It will be further observed that the tip means 20 is elongated and arranged to be received within the bore of the hollow needle shaft, particularly within the hub 17 and the shank portion as well. The bore 25 may be exceptionally small, and in particular, small relative to the inner diameter of the hollow needle 15. This prevents the biopsy specimen from entering the syringe. For example, this diameter may range from about 20% and 30% of the diameter of the shank of needle 15, the needle shank commonly having an inner diameter of about 0.05 inch. In the embodiment illustrated in FIGS. 10–14, the biopsy specimen is prevented from entering the zone which provides communication between the interior of the needle shank and the barrel chamber.

With continued attention being directed to FIGS. 1–4, it will be observed that plunger 12 is secured to gripping shaft 30, with gripping shaft 30 extending outwardly from the barrel and terminating in disk 31. FIG. 3 illustrates the gripping shaft 30 having an irregular external periphery or configuration, with the cross-section including a central shaft portion 33 along with a pair of radially extending ears 34—34. The shaft portion 33 along with the ears 34—34 are arranged to be received within the confines of bore 35 formed in plate 36, with the bore 35 including a central open portion along with radially extending members 34—34. The purpose for utilizing or providing the radially extending ears 34—34 will be made manifest hereinafter. With continued attention being directed to FIGS. 2 and 3, it will be seen that the radially extending ears 34—34 are provided for the purpose of engaging member 36 and holding or otherwise retaining the gripping shaft 30 in partially retracted position. This partially retracted disposition enables the user to reduce the pressure within the barrel 11, and thus establish a partial vacuum in the chamber communicating with needle 15. This partial vacuum assists in retracting the biopsy sample from the organ being examined, such as a sample 37, into the confines of needle 15.

As has been indicated, the technique normally employed in connection with the devices shown in FIGS. 1–4 is to initially advance the needle 15 into the body of the patient from which the biopsy sample is to be obtained, with the advancement of the needle continuing until a point is reached immediately adjacent or short of the pertinent organ. The gripping shaft is then retracted to a point at which the lugs will lock onto the surface of member 36, and the shaft is then rotated arcuately so as to engage the member 36 with the individual elements 34—34. The chamber 13 disposed within the barrel 11 is thereby evacuated and a partial vacuum is formed. The needle is then advanced further with a stabbing motion so as to contact or penetrate the pertinent organ, whereupon, when needle advancement ceases, the sample is extracted from the organ and drawn into the confines of the needle 15. Such a sample is shown at 37, as indicated in FIG. 4.

The remaining figures are provided for the purpose of illustrating modified forms of gripping shaft retention means. These various gripping shaft retention means are, of course, useful in connection with the modified structure illustrated in FIGS. 10–14 as well. With attention being directed to FIGS. 5 and 5A, the biopsy aspirating device generally designated 50 is provided with a barrel 51 and needle 52, along with a plunger (not indicated) and a gripping shaft 53. Spreader member 54 is utilized to retain the gripping shaft in retracted disposition in order to maintain the partial vacuum present within the confines of the barrel 51. Member 54 is provided with a pair of shaft gripping segments 55 and 56, spaced apart by a connecting bar 57.

The structure shown in FIGS. 6, 6A, 6B and 7 is essentially similar to that illustrated in FIGS. 1–4, with the exception of the plunger structure. In this device, the biopsy aspirating device generally designated 60 includes a barrel member 61 along with the hollow needle 62, with the plunger member 63 (see FIG. 7) being attached to gripping shaft generally designated 64. Gripping shaft 64 comprises a pair of right angularly disposed members 65 and 66, of generally rectangular configuration, and having a plurality of spaced notches such as the notches 67—67 formed therewithin. These notches will permit withdrawal of the gripping shaft and associated plunger from the barrel, with arcuate twisting permitting locking of the structure in the locking teeth 68—68, as shown in FIG. 6B.

Attention is now directed to FIGS. 8, 8A and 9 wherein a still further modification is illustrated. In this structure, the biopsy aspirating device generally designated 70 includes a barrel member 71 to which is attached the sample-receiving hollow needle 72, the structure being provided with the conventional plunger such as the plunger 63 (FIG. 7) to which is secured the gripping shaft generally designated 74. Shaft 74 is provided with a pair of longitudinally extending grooves 75 and 76, along with a pair of peripheral grooves 77 and 78. Locking teeth or ears 79—79 are provided in the body of barrel 71 in order to engage the peripheral grooves 77 and 78.

In each of the structures illustrated in FIGS. 5–9 inclusive (which structures are adaptable for use in connection with those devices illustrated in FIGS. 1–4 inclusive as well as those illustrated in FIGS. 10–14 inclusive), the structures are adapted to perform the biopsy technique previously discussed, that is, by initially penetrating the body and then establishing a partial vacuum within the chamber of the syringe barrel, and thereafter advancing the needle with a stabbing thrust, thereby extracting the tissue from the pertinent organ. Each structure is provided with means for releasably locking or releasably securing the gripping shaft in partially or fully extended disposition, so as to control the degree of partial vacuum within the confines of the chamber formed within the barrel prior to the final needle advance.

For achieving the results with the structure of the present invention, and with particular attention being directed to FIGS. 1, 4, 10 and 14, the tip end of the needle shank is tapered inwardly, as illustrated at 16 in FIG. 1, this inward tapering being accomplished in order to provide a wider receptacle area in the bore for the sample than is available at the tip or cutting edge. In this connection, a tapering angle of between about 5° and 15° is considered optimum.

Particular attention is now directed to FIGS. 10–14 of the drawings for a description of the modified form of device illustrated. The biopsy aspirating device generally designated 100 includes a barrel member 101 having a plunger 102 sealingly received within the barrel and forming a chamber zone as at 103. A sample-receiving hollow needle 105 is provided having a sharpened tip 106 and a hub 107 for locking onto the tip end of the barrel 101 with the sample-receiving hollow needle 105 having a shank portion interposed between the sharpened tip 106 and the hub 107.

A needle mounting boss means 110 is arranged at the distal or tip end of barrel 101, with the boss means 110 extending from the barrel with needle hub-receiving surface 111 being disposed therealong. In addition, boss 110 includes a projecting tip means 112 having an abutment surface 113 arranged at the free distal end thereof. This abutment surface is generally flat and planar, and is arranged to eliminate exposure of the sample 114 to unusual concentrations of pressure or forces. It will be appreciated, therefore, that annular zone 115 is provided about the outer diameter of element 112 and between the inner surface of hollow needle 105 and outer surface of element 112. A bore 117 extends between chamber 103 and the annular zone 115 to provide communication between the interior of the needle 105 and the chamber 103.

Therefore, abutment surface 113 provides a blocking means to effectively prevent continued inner movement of tissue sample 114 without blocking the air flow channel with a small or minimal area of contact. This abutment surface further is useful in preventing the transfer of any portion of the tissue sample 114 to the interior of chamber 103 under the influence of vacuum.

With continued attention being directed to FIGS. 11, 12 and 13, it will be observed that plunger 102 is secured to gripping shaft 120, with gripping shaft 120 extending outwardly from the barrel and terminating in disk 121. A plurality of notches 122—122 are formed along the surface of radially extending blades 123, 124, 125, and 126 with these notches permitting controlled withdrawal of the gripping shaft and associated plunger from the barrel, with arcuate twisting permitting locking of the structure in the locking lugs 127 and 128, as illustrated in FIG. 13. In the disposition illustrated in FIG. 12, the notches 122—122 are shown in engagement with surfaces 127 and 128 respectively, with the solid portion of the individual radially extending members 123–126 inclusive being held against abutment surfaces 129 and 130. These surfaces are illustrated in detail in FIG. 13.

As is apparent, the modification illustrated in FIGS. 10–14 inclusive provides a modified form of abutment surface as well as a modified form of providing a bore which provides communication between the interior of chamber 103 and the interior of needle 105. This is accomplished without exposing the biopsy sample to risk of damage due to inadvertent introduction of the sample 114 through a communicating conduit. As such, the structure illustrated in FIGS. 10–14 is particularly adapted for use in connection with fragile organ structures.

Attention is now directed to FIGS. 15 and 16 of the drawings wherein a still further modified form of barrel boss-needle-abutment surface arrangement is illustrated. In this modification, the needle mounting boss means 132 is arranged at the distal or tip end of barrel 133, with the boss means 132 extending from the barrel and with a needle hub-receiving surface 134 being disposed therealong. Boss 132 has a bore formed therein as at 135, with an abutment surface 136 being arranged at the distal end of boss 132. In this arrangement, bore 135 is angularly disposed relative to abutment surface 136 so as to provide a "blocking means" which prevents the biopsy sample from making contact with the passageway or bore which provides communication between the plunger chamber and the interior of the needle. As such, exposure of the sample to an unusual concentration of forces or pressures is avoided.

FIG. 16 illustrates certain of the details of the structure with the needle having been removed therefrom for purposes of clarity of detail. The structure of FIG. 16 is accordingly that of FIG. 15 with the distinction being that the needle has been removed.

The operational features and characteristics of the embodiment illustrated in FIGS. 15 and 16 will, of course, be identical to that discussed in connection with the devices illustrated in FIGS. 1–14 hereinabove.

Conventional materials of construction may be employed in these devices, with conventional plastic molded barrels and gripping shafts being desirable. Rubber plugs may be employed for the plunger means, and normal needle materials may be employed for the sample-receiving needle structures. For a general structure having substantial versatility and utility, tubing having an outer diameter of 1.4 mm, with a wall thickness of 0.004 inch has been found to be desirable.

I claim:

1. Biopsy aspirating means for gathering soft tissue samples comprising:
   a. syringe means having a barrel having a proximate end and a tip end, a plunger sealingly received within such barrel and forming a controllably variable volume chamber, an elongated sample-receiving hollow needle mounted upon said barrel, with said needle having a sharpened piercing tip at the outer end and a mounting hub at the inner end thereof, and needle mounting boss means formed integrally in one piece with said barrel as an extension thereof and being disposed at the tip end of said barrel and having a shank portion extending from the tip end of said barrel and having a means for receiving the mounting hub of said sample-receiving needle adjacent the tip end of said barrel;
   b. a gripping shaft coupled to said plunger and extending outwardly from the proximate end of said barrel, guide plate means disposed at the proximate end of said barrel and having an opening formed therein to receive said gripping shaft, said gripping shaft having locking lug means formed thereon and arranged to releasably engage the outer surface of said guide plate means for restraining inward travel of said plunger when disposed at a position removed from said barrel tip end;
   c. said needle mounting boss means terminating in an axially disposed sample abutment surface, an axial bore formed within said needle mounting boss and providing communication between the variable volume chamber of said barrel and the bore of said hollow needle shaft, said axially disposed abutment surface being received within the bore of said hollow needle and being disposed along said needle shaft at a point inwardly from the piercing tip end of said needle and toward the inner end thereof.

2. The means for gathering soft tissue biopsy samples as defined in claim 1 and being particularly characterized in that said needle mounting boss means is compressible for grippingly engaging the inner diameter of the mounting hub of said needle.

3. The means for gathering soft tissue biopsy samples as defined in claim 1 being particularly characterized in that said locking lug means on said gripping shaft are radially spaced, and radially spaced locking lug means are formed on the outer surface of said guide plate for lockingly engaging the radially spaced locking lugs formed on said gripping shaft and wherein the radial spacing of each of said locking lug means facilitates free axial motion in one relative radial disposition, with locking being established between said gripping shaft and said guide plate in a second relative radial disposition.

4. The means for gathering soft tissue biopsy samples as defined in claim 3 being particularly characterized in that the locking lug means on said gripping shaft are radially extending ears, and the locking lug means on said guide plate are radially extending slots adapted to receive the locking lug means of said gripping shaft.

5. The means for gathering soft tissue biopsy samples as defined in claim 3 being particularly characterized in that the locking lug means on said guide plate are radially extending ears, and the locking lug means on said gripping shaft are radially spaced slots arranged at axially spaced dispositions along said gripping shaft.

6. The means for gathering soft tissue biopsy samples as defined in claim 1 and being particularly characterized in that the bore formed in said needle mounting boss means has a diameter approximately 20% to 30% of the inner diameter of the shank portion of said sample-receiving hollow needle.

* * * * *